(12) United States Patent
Levinson

(10) Patent No.: US 11,925,433 B2
(45) Date of Patent: Mar. 12, 2024

(54) SYSTEM AND METHOD FOR IMPROVING AND ADJUSTING PMC DIGITAL SIGNALS TO PROVIDE HEALTH BENEFITS TO LISTENERS

(71) Applicant: DANIEL HERTZ S.A., Geneva (CH)

(72) Inventor: Mark Levinson, Geneva (CH)

(73) Assignee: DANIEL HERTZ S.A., Geneva (CH)

( * ) Notice: Subject to any disclaimer, the term of this patent is extended or adjusted under 35 U.S.C. 154(b) by 685 days.

(21) Appl. No.: 16/932,235

(22) Filed: Jul. 17, 2020

(65) Prior Publication Data

US 2022/0015633 A1    Jan. 20, 2022

(51) Int. Cl.
*G16H 10/20*    (2018.01)
*A61B 5/00*    (2006.01)
(Continued)

(52) U.S. Cl.
CPC ............ *A61B 5/002* (2013.01); *A61B 5/0004* (2013.01); *G06F 3/165* (2013.01); *G10H 1/0041* (2013.01);
(Continued)

(58) Field of Classification Search
CPC ..... A61B 5/0004; A61B 5/002; A61B 5/0244; A61B 5/4812; A61B 5/02444; A61B 5/486; A61B 5/681; A61B 7/003; A63F 13/533; A63F 13/217; G06F 3/013; G06F 3/015; G06F 3/165; G06F 3/04842; G10H 1/0041; G10H 1/46; G10K 11/002; G10L 19/018; G10L 19/0212; G10L 21/038; G16H 10/20; G16H 40/63; H03G 5/165; H03G 9/005; H04H 60/33; H04N 7/141; H04R 3/04; H04R 2430/01; A61M 21/02; H04S 7/304

See application file for complete search history.

(56) References Cited

U.S. PATENT DOCUMENTS 4,823,391 A * 4/1989 Schwartz ............... H03G 5/165
                                                 381/103
6,014,432 A * 1/2000 Modney ................. H04N 7/141
                                                 348/E7.078
(Continued)

*Primary Examiner* — Gerald Gauthier
(74) *Attorney, Agent, or Firm* — Cowan, Liebowitz & Latman, P.C.

(57) ABSTRACT

The present invention is a system and a method for processing and adjusting the PCM digital audio signals using specific reverberation and equalization settings that have been determined to potentially improve certain physical health parameters measurements, as determined by conducting bio-signal testing. The system includes a source of audio signals, producing an analog audio signal as input; a digital to analog converter, converting the analog audio signal to digital; a digital system processor, having a computer processor and memory or circuitry for processing the input audio signal using an equalization, a reverberation and a volume setting that is measured to produce an audio output signal that has more beneficial health response on human physiological functions than an unprocessed PCM digital signal or a base measurement without any audio signal, as measured by at least one bio-sensor attached to at least one listener. As a result, the present invention improves at least one physiological function of the listener, as measured using bio-sensors in the Avatar health testing bio-sensor measuring system.

11 Claims, 5 Drawing Sheets

(51) Int. Cl.
*G06F 3/16* (2006.01)
*G10H 1/00* (2006.01)
*G10H 1/46* (2006.01)
*G10K 11/00* (2006.01)
*H03G 9/00* (2006.01)

(52) U.S. Cl.
CPC ............. *G10H 1/46* (2013.01); *G10K 11/002* (2013.01); *G16H 10/20* (2018.01); *H03G 9/005* (2013.01)

(56) References Cited

U.S. PATENT DOCUMENTS

| | | | | |
|---|---|---|---|---|
| 7,346,174 | B1* | 3/2008 | Smith | G16H 40/63 600/528 |
| 10,043,527 | B1* | 8/2018 | Gurijala | G10L 19/018 |
| 2005/0113167 | A1* | 5/2005 | Buchner | A63F 13/285 463/30 |
| 2009/0018456 | A1* | 1/2009 | Hung | A61B 5/681 600/509 |
| 2011/0274013 | A1* | 11/2011 | Gass | A61B 5/002 370/259 |
| 2012/0184825 | A1* | 7/2012 | Ben David | A61B 7/003 607/42 |
| 2012/0221326 | A1* | 8/2012 | Grancharov | G10L 21/038 704/205 |
| 2015/0046496 | A1* | 2/2015 | Karmarkar | G06F 3/013 707/798 |
| 2016/0378427 | A1* | 12/2016 | Sharma | G10L 19/0212 700/94 |
| 2018/0097975 | A1* | 4/2018 | Osman | A63F 13/533 |
| 2019/0321583 | A1* | 10/2019 | Poltorak | A61M 21/02 |
| 2020/0159323 | A1* | 5/2020 | Gand | G06F 3/04842 |
| 2020/0260209 | A1* | 8/2020 | Yadegari | H04S 7/304 |
| 2020/0405212 | A1* | 12/2020 | Chappell, III | H04H 60/33 |
| 2021/0000347 | A1* | 1/2021 | Stump | A61B 5/02444 |
| 2021/0298676 | A1* | 9/2021 | Shriner | A61B 5/4812 |
| 2022/0015633 | A1* | 1/2022 | Levinson | G10H 1/46 |
| 2023/0047787 | A1* | 2/2023 | Chappell, III | G06F 3/015 |

* cited by examiner

AVATAR TEST
UMU Processing

420 — No music (baseline test): acceptable measurements
430 — Listening to PCM digital audio: severely degraded measurement
440 — With UMU processing, listening to music, health is improved compared to listening to no music.

Test #1 (410)

Session description:
Subject 1
Session Notes: Mark Levinson
Hold Tray Items:

| Point | Item |
|---|---|
| RHBND 1b CMP[R] | [Right Hand Back: Central Nervous System CMP] |
| RF Lv1a CMP[R] | [Right Foot: Liver CMP] |
| RA KI3 [R] | [Right Ankle: Renal Cortex] |

461:
| Graph | Peak | Drop |
|---|---|---|
| | 67.1 | 2.0 |
| | 75.7 | 2.4 |
| | 69.7 | 1.0 |

Session description:
Subject 1
Session Notes:
Hold Tray Items:

| Point | Item |
|---|---|
| RA KI3 [R] | [Right Ankle: Renal Cortex] |
| RF Lv1a CMP[R] | [Right Foot: Liver CMP] |
| RHBND 1b CMP[R] | [Right Hand Back: Central Nervous System CMP] |

462:
| Graph | Peak | Drop |
|---|---|---|
| | 14.4 | 0.9 |
| | 44.5 | 2.0 |
| | 40.9 | 1.1 |

Session description:
Subject 1
Session Notes:
Hold Tray Items:

| Point | Item |
|---|---|
| RHBND 1b CMP[R] | [Right Hand Back: Central Nervous System CMP] |
| RF Lv1a CMP[R] | [Right Foot: Liver CMP] |
| RA KI3 [R] | [Right Ankle: Renal Cortex] |

463:
| Graph | Peak | Drop |
|---|---|---|
| | 53.9 | 1.0 |
| | 55.5 | 2.0 |
| | 52.4 | 1.5 |

Test #2 (412)

Session description:
Subject 2
Session Notes: Mark Levinson
Hold Tray Items:

| Point | Item |
|---|---|
| RHBND 1b CMP[R] | [Right Hand Back: Central Nervous System CMP] |
| RF Lv1a CMP[R] | [Right Foot: Liver CMP] |
| RA KI3 [R] | [Right Ankle: Renal Cortex] |

471:
| Graph | Peak | Drop |
|---|---|---|
| | 79.9 | 2.7 |
| | 85.5 | 1.2 |
| | 81.3 | 2.6 |

Session description:
Subject 2
Session Notes:
Hold Tray Items:

| Point | Item |
|---|---|
| RHBND 1b CMP[R] | [Right Hand Back: Central Nervous System CMP] |
| RF Lv1a CMP[R] | [Right Foot: Liver CMP] |
| RA KI3 [R] | [Right Ankle: Renal Cortex] |

472:
| Graph | Peak | Drop |
|---|---|---|
| | 35.2 | 1.3 |
| | 91.1 | 1.3 |
| | 29.9 | 1.6 |

Session description:
Subject 2
Session Notes:
Hold Tray Items:

| Point | Item |
|---|---|
| RHBND 1b CMP[R] | [Right Hand Back: Central Nervous System CMP] |
| RF Lv1a CMP[R] | [Right Foot: Liver CMP] |
| RA KI3 [R] | [Right Ankle: Renal Cortex] |

473:
| Graph | Peak | Drop |
|---|---|---|
| | 51.7 | 2.0 |
| | 55.2 | 0.9 |
| | 51.0 | 2.3 |

FIG. 4A

Test #3 — 414

Session description:
Subject 3
Session Notes:
Mark Levinson
Hold Tray Items:

| Point | Item | Graph | Peak | Drop |
|---|---|---|---|---|
| RHB.ND.Ib CMP[R] | [Right Hand Back-Central Nervous System CMP] | | 69.5 | 1.9 |
| RF.Lv.Ia CMP[R] | [Right Foot-Liver CMP] | | 73.8 | 3.1 |
| RA.KI.3 [R] | [Right Ankle-Renal Cortex] | | 74.6 | 0.2 |

481 / 451 / 452 / 453

Session description:
Subject 3
Session Notes:
Hold Tray Items:

| Point | Item | Graph | Peak | Drop |
|---|---|---|---|---|
| RHB.ND.Ib CMP[R] | [Right Hand Back-Central Nervous System CMP] | | 41.2 | 1.5 |
| RF.Lv.Ia CMP[R] | [Right Foot-Liver CMP] | | 81.5 | 0.2 |
| RA.KI.3 [R] | [Right Ankle-Renal Cortex] | | 45.7 | 3.1 |

482 / 451 / 452 / 453

Session description:
Subject 3
Session Notes:
Hold Tray Items:

| Point | Item | Graph | Peak | Drop |
|---|---|---|---|---|
| RHB.ND.Ib CMP[R] | [Right Hand Back-Central Nervous System CMP] | | 53.8 | 2.2 |
| RF.Lv.Ia CMP[R] | [Right Foot-Liver CMP] | | 53.4 | 1.2 |
| RA.KI.3 [R] | [Right Ankle-Renal Cortex] | | 52.4 | 1.6 |

483 / 451 / 452 / 453

Test #4 — 416

Session description:
Subject 4
Session Notes:
Hold Tray Items:

| Point | Item | Graph | Peak | Drop |
|---|---|---|---|---|
| RHB.ND.Ib CMP[R] | [Right Hand Back-Central Nervous System CMP] | | 63.4 | 2.1 |
| RF.Lv.Ia CMP[R] | [Right Foot-Liver CMP] | | 79.0 | 1.5 |
| RA.KI.3 [R] | [Right Ankle-Renal Cortex] | | 80.1 | 0.7 |

491 / 451 / 452 / 453

Session description:
Subject 4
Session Notes:
Hold Tray Items:

| Point | Item | Graph | Peak | Drop |
|---|---|---|---|---|
| RHB.ND.Ib CMP[R] | [Right Hand Back-Central Nervous System CMP] | | 33.5 | 1.1t |
| RF.Lv.Ia CMP[R] | [Right Foot-Liver CMP] | | 35.4 | 1.7 |
| RA.KI.3 [R] | [Right Ankle-Renal Cortex] | | 40.1 | 2.0 |

492 / 451 / 452 / 453

Session description:
Subject 4
Session Notes:
Hold Tray Items:

| Point | Item | Graph | Peak | Drop |
|---|---|---|---|---|
| RHB.ND.Ib CMP[R] | [Right Hand Back-Central Nervous System CMP] | | 50.1 | 1.9 |
| RF.Lv.Ia CMP[R] | [Right Foot-Liver CMP] | | 53.0 | 1.7 |
| RA.KI.3 [R] | [Right Ankle-Renal Cortex] | | 57.9 | 0.1 |

SYSTEM AND METHOD FOR IMPROVING AND ADJUSTING PMC DIGITAL SIGNALS TO PROVIDE HEALTH BENEFITS TO LISTENERS

TECHNICAL FIELD

The present invention relates to digital audio signals and signal processing. In particular, it relates to PCM digital audio improvements and using specific reverberation and equalization settings that have been determined to potentially improve certain physical health parameters measurements and the listening experience of anyone who listen to the sound.

BACKGROUND

Many known systems and methods allow users to conveniently control characteristics of sounds generated by musical instruments or recorded speech. Generally, the systems include a computer processor, having a memory that stores computer instructions or includes circuitry that control communication with any number of audio processing devices ("APDs"), which receive sampled analog signals representing a particular sound (for example, a song, music, soundtrack or human speech). Many known audio systems also utilize Pulse-code modulation (PCM) as a method used for digitally representing sampled and converted analog signals, received as input.

The first PCM-based recorders were developed in the later part of the 1960s, and stored digital recordings of audio signals on a video tape recorder or other digital media that allowed storage of digitized binary data that represented analog sound that has been converted to digital form. In the late mid-1970s and early 1980s, compact discs (CDs) were developed, and utilized PCM processing for storing digital pop and other music, which could then be purchased and enjoyed by consumers.

In the computer field, PCM-based digital telephony was developed in the 1970s, which also led to the development of PCM code-filter-chips (in late 1970s). The PCM chips were used in computers and later in telecommunication networks that transmit audio data as packets or streams over computer networks. This allowed easy and efficient transmission and sharing of the audio and audio-video files, such as streaming videos, audio files, digital music, digitized voice communications and other sound and voice related applications.

The PCM-based digital audio is currently used in most telephony, video and Internet transmissions and audio applications. While there is some variation in sampling rate for the conversion of the analog audio signals to the digital format, the most current systems receive and process digitized audio data generally based on the PCM process developed in the 1970s.

In other words, there have been no fundamental improvements to the basic PCM technology. Formats with more bits and bandwidth have been added, but the PCM mechanism (analog to digital, and digital to analog conversions) have remained generally unchanged to present time. Some forms of PCM combine signal processing with coding and compression.

SUMMARY OF THE INVENTION

When comparing the digitized audio with analog signals, many recording engineers and musicians have complained over the course of the last 40 years that PCM-transformed digital audio and sound is fatiguing and much less enjoyable than analog audio, where the audio signals are not transformed to a digital format. The inventor of the present invention addressed this problem by undertaking a scientifically-based study and analysis of the physical as well as psychological effects of the PCM-transformed digital audio signals on the listeners.

The computer devices, digital phones/telephony and other known digital audio applications and devices receive analog data that represents input sound and convert it to a digital format. In a PCM stream, the amplitude of the analog signal may be sampled regularly at some (preferably uniform intervals), and each sample is quantized to the nearest value within a range of digital steps.

One feature of the present invention is an audio processing computerized system for processing of audio signals that includes (1) a source of audio signals, producing an analog audio signal as input; (2) a digital to analog converter, converting the analog audio signal to digital; (3) a digital system processor, having a computer processor and memory or circuitry for processing the input audio signal using an equalization, a reverberation and a volume setting that is measured to produce an audio output signal that has more beneficial health response on human physiological functions than an unprocessed PCM digital signal or a base measurement without any audio signal, as measured by at least one bio-sensor attached to at least one listener. One of the features and results of the present invention is a quantifiable improvement of at least one physiological function of the listener.

The system may also include a number of bio-sensors attached to the at least one listener, to measure the bio-signal response related to a central nervous system, a liver or a kidney function of the listener. The bio-signal responses related to the central nervous system, the liver and the kidney function of the listener using at least one embodiment produce results in in the range of 50-60 using the Avatar health testing bio-sensor measuring system.

Another feature of the present invention is applying the reverberation settings that include a reverberation time period in a range from about 0.05 to 0.5 seconds in at least one embodiment. In other embodiments, the reverberation time may be set to 0.1 seconds or near it (within −0.02 to +0.2 seconds range).

An additional feature of the present invention is an HF damping setting that is in a range from about 6 to 8 kHz in at least one embodiment. In other embodiments, the HF damping setting may be set at 7500 Hz (7.5 kHz) or near it (within −1 to +1 kHz range).

A further feature of the present invention is applying the reverberation amplitude setting that includes a dry reverberation setting in a range from about −0.1 to −2.0 dB range in at least one embodiment. In other embodiments, the dry reverberation rate may be set to −0.25 dB or near it (within −0.05 to +0.25 dB range).

Yet another feature of the present invention is applying a wet reverberation setting is in a range from −99.9 to −97.9 dB in at least one embodiment. In other embodiments, the wet reverberation setting may be set to −99.683 dB or near it (within −0.5 to +0.1 dB range).

A further feature of the present invention is also applying equalization settings, with Q setting at −0.26 or near it, a 40 Hz frequency setting at +0.2 dB or near it, a 2 kHz frequency setting at −0.2 dB or near it, and a 12 kHz frequency setting at +0.2 dB or near it.

One or more additional features of the present invention in at least one alternative embodiment may include the following Reverb settings:

(a) a Pre-Delay setting in a range from 40 to 120 ms, and may use a default setting for Pre-Delay at 100.8 ms or near it.

(b) a Delay time setting in a range from 0.01 to 0.99 sec., and may use a default setting for Delay time setting at 0.32 sec or near it.

(c) a Direct Signal to Early Signal Ref ratio in a range from 20 to 80%, and may use a default setting at 57.2% or near it.

(d) a Tail Decay setting in a range from 0.10 to 2.0%, and may use a default setting at 0.64% or near it.

(e) an Early Ref. Reverb Level in a range from −30 to 0 dBFS, and may use a default setting at 0 dBFS or near it. The dBFS refers to Decibels relative to full scale, which is a unit of measurement for amplitude levels in digital audio systems.

(f) a Tail Level for Reverb in a range from −25 to 0 dBFS, and may use a default setting at −10.4 dBFS or near it.

(g) a Wet to Dry signal ratio in a range from 0 to 35%, and may use a default setting at 1% or near it.

(h) a Damping Freq. Low in a range from 50 to 500 Hz, and may use a default setting at 302 Hz or near it.

(i) a Damping Freq. High in a range from 5000 to 14,000 Hz, and may use a default setting of 7854 Hz or near it.

(j) a Filter Center Freq. in a range from 8000 to 16,000 Hz, and may use a default setting of 10300 Hz or near it.

(k) a Filter Gain in a range from −4 to −25 dBFS, and may use a default setting of −18.8 Hz or near it.

Yet one or more additional features of the present invention in at least one additional embodiment may include the following Reverb settings:

(a) a Pre-Delay setting in a range from 40 to 120 ms, and may use a default setting for Pre-Delay at 100.8 ms or near it.

(b) a Delay time setting in a range from 0.01 to 0.99 sec., and may use a default setting for Delay time setting at 0.32 sec or near it.

(c) a Direct Signal to Early Signal Ref ratio in a range from 20 to 80%, and may use a default setting at 57.2% or near it.

(d) a Tail Decay setting in a range from 0.10 to 2.0%, and may use a default setting at 0.64% or near it.

(e) an Early Ref. Reverb Level in a range from −30 to 0 dBFS, and may use a default setting at 0 dBFS or near it. The dBFS refers to Decibels relative to full scale, which is a unit of measurement for amplitude levels in digital audio systems.

(f) a Tail Level for Reverb in a range from −25 to 0 dBFS, and may use a default setting at −10.4 dBFS or near it.

(g) a Wet to Dry signal ratio in a range from 0.1 to 20%, and may use a default setting at 1% or near it.

(h) a Damping Freq. Low in a range from 50 to 500 Hz, and may use a default setting at 302 Hz or near it.

(i) a Damping Freq. High in a range from 5000 to 14,000 Hz, and may use a default setting of 6000 Hz or near it.

(j) a Filter Center Freq. in a range from 80 to 300 Hz, and may use a default setting of 166 Hz or near it.

(k) a Filter Gain in a range from −2 to 2 dBFS, and may use a default setting of 0.5 dBFS or near it.

A Filter Type for these Reverb setting may be a "shelf filter" and the Reverb type may be "room".

Another features of the present invention in at least one alternative embodiment include the following EQ settings:

(a) a Gain in a range from 0.1 to 1 dB, and may use a default setting for Gain at 0.1 dB or near it.

(b) a Center Freq. in a range from 4000 to 6000 Hz, and may use a default setting at 5000 Hz or near it.

(c) a Quality Factor in a range from 0.10 to 1.0 Q, and may use a default setting at 0.26 Q or near it.

A Filter Type for these EQ setting may be a "bell" filter.

Another feature of the present invention is also including a synthesizer or a controller for processing audio signals from a source of audio signals as part of the overall system.

Yet another feature of the present invention is also including a digital to analog converter, for converting the processed digital audio signals to analog and an output device for producing the analog audio output based on the processed audio signals as part of the overall system.

The present invention may utilize a number of different digital data formats for the input data that undergoes the equalization, the reverberation and the volume settings transformations in accordance with the present invention. These data format may be a WAV, AIFF or MP3 digital data format. The same data formats may be utilized for the transmission of the output data to another audio or computer device.

These and other beneficial features and advantages of the present invention are disclosed in detail hereinafter with reference to the accompanying drawings and description of various embodiments and features of the present invention.

BRIEF DESCRIPTION OF THE DRAWINGS

FIGS. 4A and 4B are charts of a pilot Avatar Test conducted on individuals in three control groups, and assessing function of liver, kidneys and central nervous system in the group using the PCM-digitized signals and modified signals in accordance with at least one embodiment of the present invention.

DETAILED DESCRIPTION OF THE INVENTION

In at least one embodiment, the present invention relates to methods and systems for controlling characteristics of sounds that may be generated by audio devices, such as musical instruments or audio sounds recorded through a microphone, where the analog sounds are processed by any type of PCM or similar analog-to-digital conversion into a digitized audio data.

Figure 1:
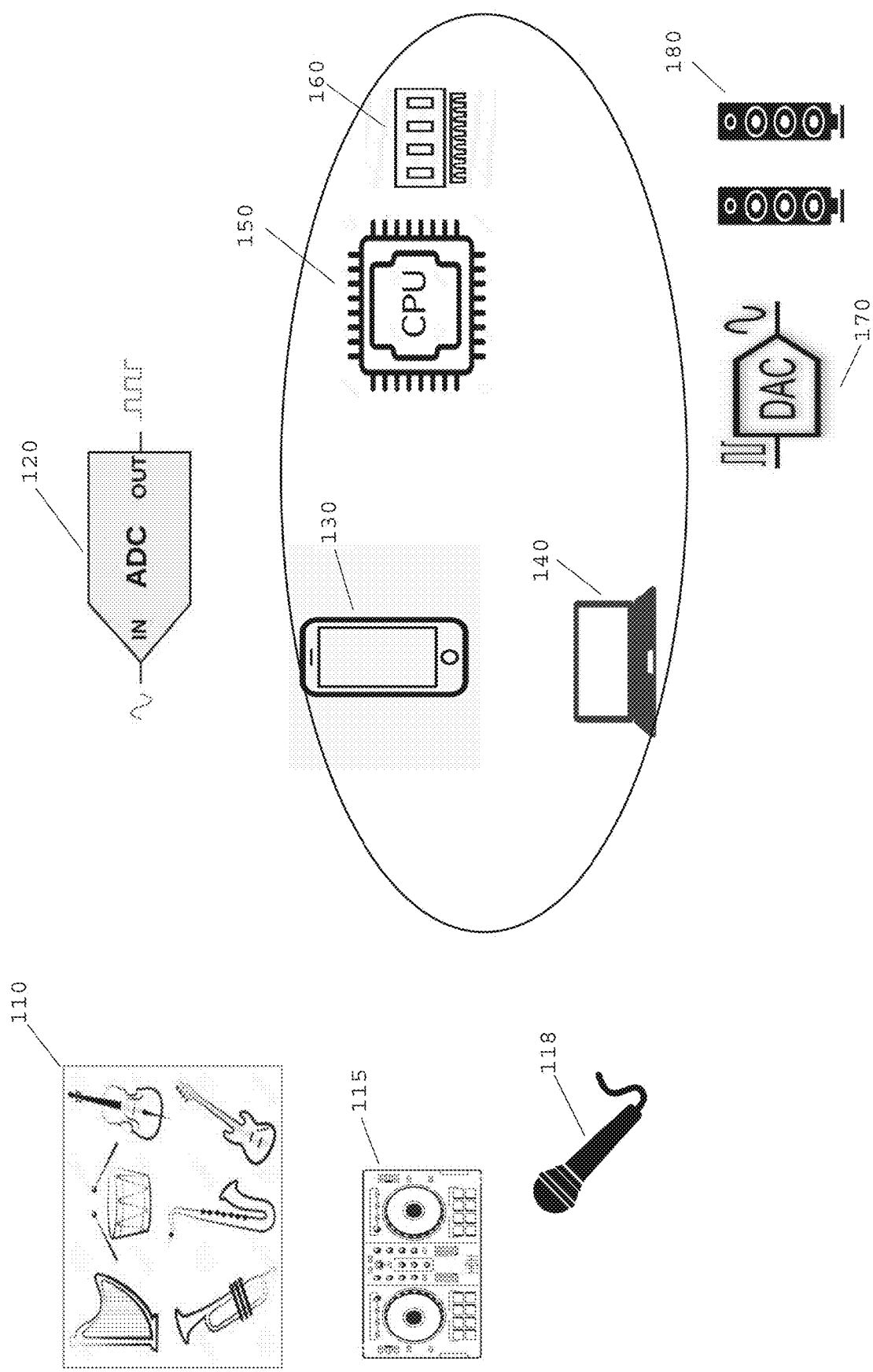
FIG. 1 illustrates a general system and components of the system that may utilize the present invention and operate in accordance with at least one embodiment.

Referring to FIG. 1, an audio input signal or sound 110 is generated by a person or a musical instrument, such as, for example, a guitar, violin, piano, keyboard, drums, winds, other instruments or a synthesizer, DJ-controller 115, or generated by a computer or an audio input device, like a microphone 118. The generated audio input signal or sound 110 could be analog or digital. If it is analog, will typically undergo conversion from analog-to-digital as part of a PCM process 120 in a synthesizer, mixer or digital processor, or through a codec in a mobile phone 130, a computer device 140 or any type of an audio signal input processing device with digital signal processing capabilities. The conversion from analog-to-digital may be done by a software codec, executed by a processor 150, which executes computer instructions stored in computer memory 160.

Alternatively, the analog-to-digital conversion could be performed by a hardware codec or circuitry 170 (not shown), which might operate as an application-specific integrated circuit (ASIC) in the audio input device, or in the computer, mobile phone, synthesizer, DJ-controller or other similar audio processing devices. An application-specific integrated circuit is an integrated circuit (IC) chip customized for a particular use, rather than intended for general-purpose use. For example, a chip designed to run in a digital voice recorder is an ASIC.

The computer devices, digital phones/telephony and other known digital audio applications and devices could receive and process analog audio data that represents input sound through a microphone and convert it to a digital format. Alternatively, the audio input devices may receive already digitized audio signal as input.

Figure 2:
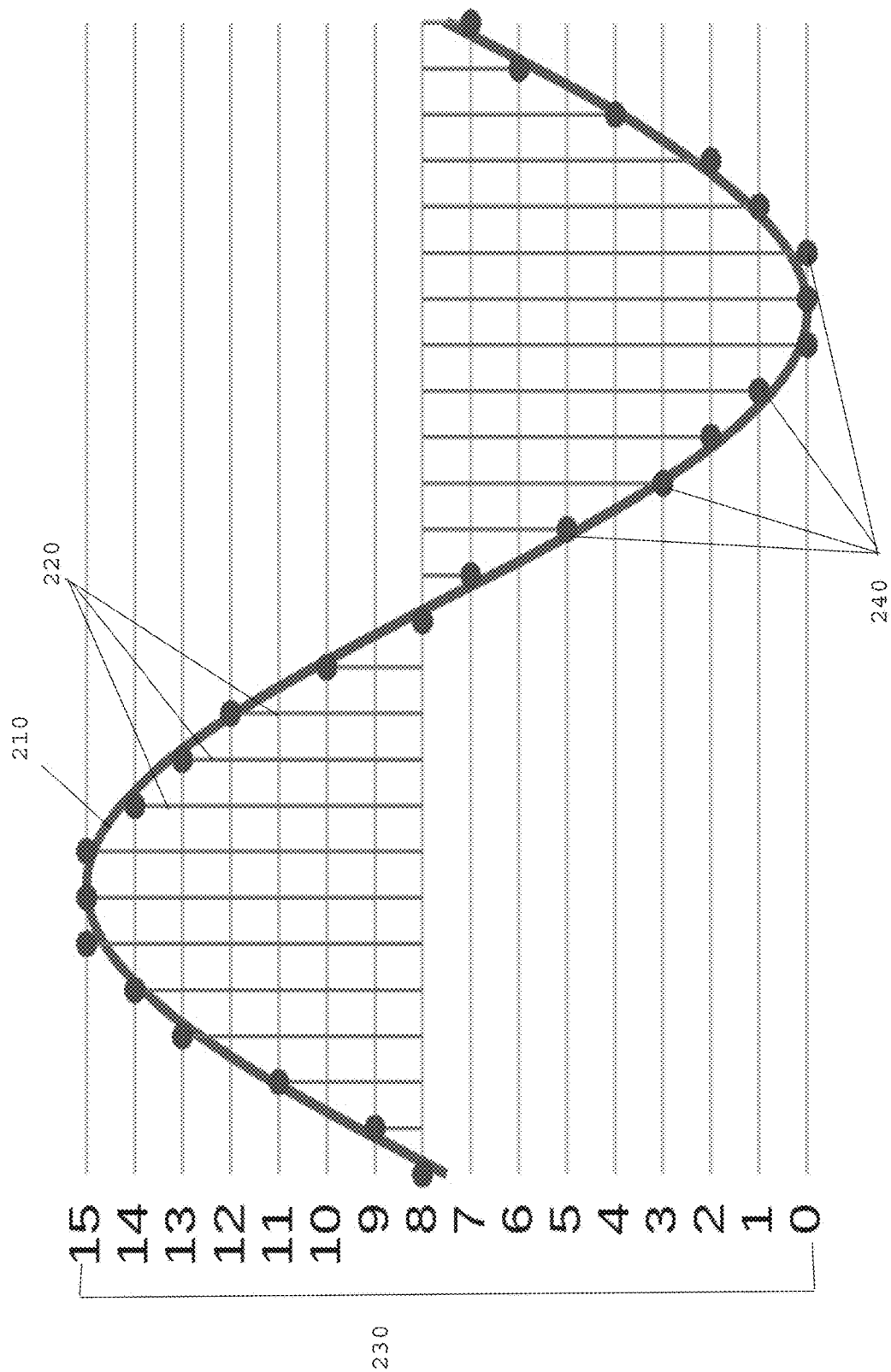
FIG. 2 illustrates a general method of sampling and quantization of an audio signal for a 4-bit linear PCM transformation of an audio signal.

In a PCM stream, the amplitude of the analog signal may be sampled regularly at some (preferably uniform intervals), and each sample is quantized to the nearest value within a range of digital steps. Modulation and analog to digital conversion of an audio signal is described with reference to FIG. 2, which illustrates an example of sampling and quantization of an audio signal 210 for 4-bit linear PCM process.

An audio signal 210 is in a form of a sine wave, which is sampled at regular intervals, shown as vertical lines 220. For each sample, one of the available values 230 (on the y-axis) is chosen. The PCM process is commonly implemented on a single IC called an analog-to-digital converter (ADC). As a result of the process, a fully discrete digital representation of the input digital signal 240 (a few examples are marked) can be easily encoded as digital data 250 (not shown) for storage or manipulation. This digitized audio signal can be further processed, compressed, transferred or stored on a digital media for replay or transmission over the network.

Several PCM streams could also be multiplexed into a larger, aggregate data stream, generally for transmission of multiple streams over a single physical link. One such known technique is called time-division-multiplexing and is widely used, notably in the modern public telephone system.

The digital signal may also be converted back to analog through a digital-to-analog converter 170 (DAC) for reproduction. For example, the digitized audio is converted from the digital data to an analog sound for replaying audio signals through one or more speakers 180, as shown in FIG. 1. The electronics involved in producing an accurate analog signal from the discrete digital data are similar to those used for generating the digital signal. The known DAC devices could be either software or hardware based. They produce a voltage or current (depending on type) that represents the value presented on their digital inputs. This output is then generally filtered and amplified through an amplifier unit (not shown) for reproduction and drive the amplitude and characteristics of the audio sound that comes through the speakers 180.

In order to restore or recreate the original audio signal from the sampled data, a demodulator can apply the procedure of modulation in reverse. After each sampling period, the demodulator reads the next value and transitions the output signal to the new value. As a result of these transitions, the signal gains a significant amount of high-frequency energy due to aliasing effects. In order to remove these undesirable frequencies, the demodulator may pass the signal through a reconstruction filter that suppresses energy outside the expected frequency range.

Figure 3:
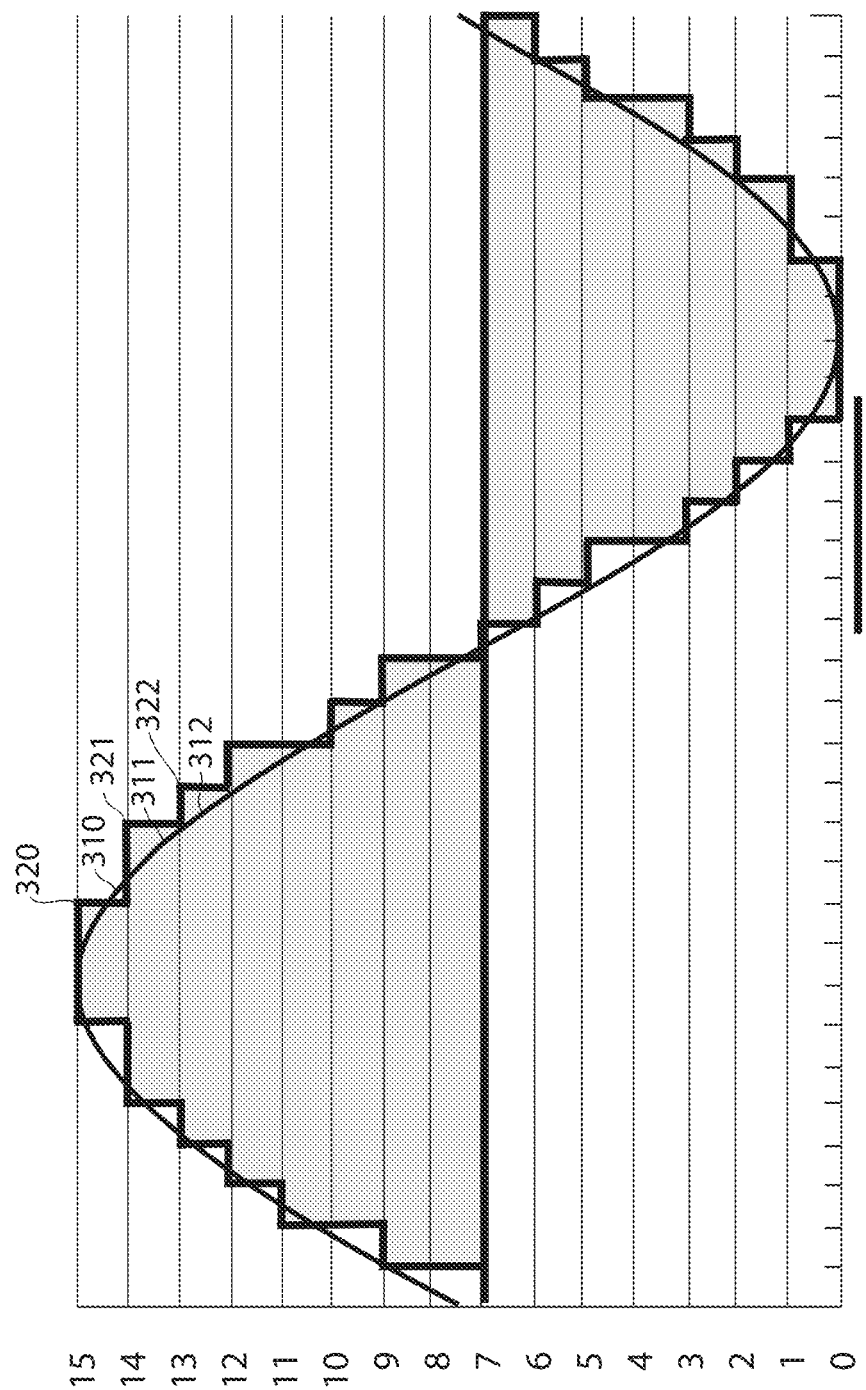
FIG. 3 illustrates a general step function that is utilized as part of general PCM transformation of an analog signal to digital format, illustrating differences between discrete digital values and the smooth audio curve.

FIG. 3 illustrates a general step function that is utilized as part of general PCM transformation of an analog signal to digital format. As shown, the digital discrete value that is utilized for the actual representation of an audio at each point 320, 321 and 322 (as examples) is an approximation of the actual audio signal at that point because of the binary (digital) nature of each digital values assigned at each discrete interval.

As a result the digitized set of values differs from the smooth audio sound at points 310, 311 and 312 (as examples). Because of this inherent difference between the original analog audio and the digitized sound, many musicians and recording engineers have often been complaining about the less pleasant listening experience when using digitized sound than when listening to the live or non-digitized sound.

In order to address these well-known complaints and concerns about digitized audio, the inventor of the present has undertaken a scientific study of bio-signals and the effects of the digitized sound on the specific bio-signals and quantifiable physiological changes in different control groups. The unusual and unexpected results using at least one embodiment of the present invention are described below with reference to FIGS. 4A and 4B.

The bio-signals are signals that are generated by biological beings that can be measured and monitored. For example, the electroencephalographs, galvanometers, and electrocardiographs are just some devices that could be used to measure and monitor bio-signals generated by humans. Other types of monitoring devices that can identify and quantify function of certain body organs or the overall nervous systems or well-being of a person could also be used.

As an example, a human brain generates bio-signals such as electrical patterns, which may be measured or monitored using an electroencephalogram (EEG). These electrical patterns, or brainwaves, are measurable by devices such as an EEG. Typically, an EEG will measure brainwaves in an analog form. Then, these brainwaves may be analyzed either in their original analog form or in a digital form after an analog to digital conversion. Measuring and analyzing bio-signals such as brainwave patterns can have a variety of practical applications.

In at least one embodiment, the measuring of the bio-signals provided unknown and unexpected results and conclusions about the use of digitized sound. It also allowed to determine and test settings that actually improve the physiological condition of, as well as overall listening experience to the PCM digital audio for, a listener in accordance with at least one embodiment of the present invention.

In accordance with at least one embodiment, the present invention utilizes the UMU technology, which improves and modifies any type of PCM digital audio to make it better for human health and overall human experience. UMU technology is based on and applies a specifically selected and unique combination of reverberation setting or a reverberation setting with a particular type of equalization setting or equalization setting range and precisely calibrated amplitude setting or setting range.

The determined settings have been tested based on several control groups and have been determined to enhance the brain response and improve several physiological components that were monitored in the control groups using bio-signal devices.

One of the features of UMU technology of the present invention is the ability to create a smooth waveform for the audio from the non-continuous sampled, PCM-processed and digitized audio signals. Referring to FIG. 3, the specific settings for reverberation and equalization utilized in at least one embodiment result in the "filling in" or adding the gaps that exist between the original smooth analog sine wave at points 310, 311 and 312 (given as examples), representing the original analog audio signal, and the corresponding discrete points 321, 322 and 322 (given as corresponding examples) that indicate the sampled PCM-processed digital audio signals. In other words, of the features of the present invention is that it fills in the spaces in the step function waveform shown in FIG. 3 with original music information, utilizing reverberations and equalization settings, without any additional sound effects, noise or non-original modifications.

Another feature of the present invention is that it is not intended to be a sound effect and produces a sonic change that is extremely subtle or inaudible to a human. In other words, the added or "filled in" audio into the gaps produce virtually no audible effect and do not alter the music or sound content.

In accordance with at least one embodiment, the present invention utilizes the following settings that may be applied as input into a digital audio processing system and provide the desired results.

TABLE 1

| Reverberation settings: | |
|---|---|
| Reverb Time | .1 s or near (for example, within −.02 to +0.2 seconds range) |
| HF Damping | 7500 Hz or near (for example, within −1 to +1 kHz range) |
| Reverberation amplitude | |
| Dry | −.25 dB or near (within −0.05 to +0.25 dB range) |
| Wet | −99.68 dB or near (within −0.5 to +0.1 dB range). |
| Equalization: | |
| Q: | .26 or near |
| 40 Hz: | +.2 dB or near |
| 2 kHz: | −.2 dB or near |
| 12 kHz: | +.2 dB or near |

The settings set forth in Table 1 may be also be utilized as default setting and changed to different settings at a later time in accordance with other embodiments. In other embodiments, the settings may vary within an indicated range, and still achieve the desired results and include the functionality of the present invention. The possible ranges for various settings in accordance with at least one embodiment of the present invention are set forth in Table 2 below. Each may be applied as input into a digital audio processing system and provide the desired results.

TABLE 2

| Reverberation settings: | |
|---|---|
| Reverb Time | in a range from 0.05 to 0.5 seconds, or near |
| HF Damping | in a range from 6 to 8 kHz, or near |
| Reverberation amplitude | |
| Dry | in a range from −0.1 to −2.0 dB, or near |
| Wet | in a range from −99.9 to −97.9 dB or near |
| Equalization: | |
| Q: | .26 or near |
| 40 Hz: | +.2 dB or near |

TABLE 2-continued

| 2 kHz: | −.2 dB or near |
|---|---|
| 12 kHz: | +.2 dB or near |

The "reverberation time" refers to a time measurement that the amount of time that it takes for the sound to "fade away" (usually in an enclosed area), measured after the source of sound has stopped. The HF Damping refers to the "high frequency damping", which is the reduction of energy or oscillation at or over certain set high frequency.

The "dry" typically refers to the input signal and "wet" to the output (effected or processed) signal, and a wet/dry setting on the mixer or amplifier will control the mix of the two. In other words, if a particular setting is set to 100% wet, it means that there is no original "dry" (input signal), and a person would typically hear only the reverberations, and not the original sound. The "Q" in the equalization settings refers to the width of the EQ band that is being adjusted. The 40 Hz, 2 kHz and 12 kHz refer to different EQ frequency settings and ranges.

Versions with a more audible effect can be created by manipulating these settings of the reverb, eq, and amplitude, and can be useful for some additional applications, and accomplish the desired results in accordance with at least one embodiment of the invention.

In accordance with at least one other embodiment, the present invention may utilizes the following settings that may be applied as input into a digital audio processing system and provide the desired results of the present invention.

TABLE 3

| Reverberation settings: | |
|---|---|
| Pre-Delay setting | 100.8 ms or near |
| Decay Time setting | 0.32 sec or near it |
| Direct Signal to Early Signal Ref. Ratio | 57.2% or near it |
| Tail Decay | 0.64% or near it |
| Early Ref. Reverb Level | 0 dBFS or near it |
| Tail Level for Reverb | −10.4 dBFS or near it |
| Wet to Dry signal ratio | 1% or near it |
| Damping Freq. Low | 302 Hz or near it |
| Damping Freq. High | 7854 Hz or near it |
| Filter Center Freq. | 10300 Hz or near it |
| Filter Gain | −18.8 Hz or near it |
| Filter Type | Shelf |
| Reverb Type | Room |
| Equalization: | |
| Gain | 0.1 dB or near it |
| Center Freq. | 5000 Hz or near it |
| Quality Factor | 0.26 Q or near it |
| Filter Type | Bell |

The settings set forth in Table 3 may be also be utilized as default setting and changed to other settings at a later time in accordance with other embodiments. In other embodiments, the settings in Table 3 may vary within an indicated range, and still achieve the desired results and include the functionality of the present invention.

The possible ranges for various settings in accordance with at least one embodiment of the present invention are set forth in Table 4 below. Each may be applied as input into a digital audio processing system and provide the desired results.

TABLE 4

| Reverberation settings: | |
|---|---|
| Pre-Delay setting | in a range from 40 to 120 ms, |
| Decay Time setting | in a range from 0.01 to 0.99 sec |
| Direct Signal to Early Signal Ref. Ratio | in a range from 20 to 80% |
| Tail Decay | in a range from 0.10 to 2.0% |
| Early Ref. Reverb Level | in a range from −30 to 0 dBFS |
| Tail Level for Reverb | in a range from −25 to 0 dBFS |
| Wet to Dry signal ratio | in a range from 0 to 35% |
| Damping Freq. Low | in a range from 50 to 500 Hz |
| Damping Freq. High | in a range from 5000 to 14,000 Hz |
| Filter Center Freq. | in a range from 8000 to 16,000 Hz |
| Filter Gain | in a range from −4 to −25 dBFS |
| Filter Type | Shelf |
| Reverb Type | Room |
| Equalization: | |
| Gain | in a range from 0.1 to 1 dB |
| Center Freq. | in a range from 4000 to 6000 Hz |
| Quality Factor | in a range from 0.10 to 1.0 Q |
| Filter Type | Bell |

In accordance with another embodiment, the present invention may utilizes the following Reverberation settings that may be applied as input into a digital audio processing system and provide the desired results of the present invention. The Equalization settings set forth in Tables 1-4 may be utilized with the Reverberation settings described below.

TABLE 5

| Reverberation settings: | |
|---|---|
| Pre-Delay setting | 100.8 ms or near |
| Decay Time setting | 0.32 sec or near it |
| Direct Signal to Early Signal Ref. Ratio | 57.2% or near it |
| Tail Decay | 0.64% or near it |
| Early Ref. Reverb Level | 0 dBFS or near it |
| Tail Level for Reverb | −10.4 dBFS or near it |
| Wet to Dry signal ratio | 1% or near it |
| Damping Freq. Low | 302 Hz or near it |
| Damping Freq. High | 6000 Hz or near it |
| Filter Center Freq. | 166 Hz or near it |
| Filter Gain | −0.5 dBFS or near it |
| Filter Type | Shelf |
| Reverb Type | Room |

The settings set forth in Table 5 may be also be utilized as default setting and changed to other settings at a later time in accordance with other embodiments. In yet other embodiments, the settings in Table 5 may vary within an indicated range, and still achieve the desired results and include the functionality of the present invention. The possible ranges for various Reverberation settings in accordance with at least one embodiment of the present invention are set forth in Table 6 below. Each may be applied as input into a digital audio processing system and provide the desired results. The Equalization settings set forth in Tables 1-4 may be utilized with the Reverberation settings described below.

TABLE 6

| Reverberation settings: | |
|---|---|
| Pre-Delay setting | in a range from 40 to 120 ms, |
| Decay Time setting | in a range from 0.01 to 0.99 sec. |
| Direct Signal to Early Signal Ref. Ratio | in a range from 20 to 80% |
| Tail Decay | in a range from 0.10 to 2.0% |
| Early Ref. Reverb Level | in a range from −30 to 0 dBFS |
| Tail Level for Reverb | in a range from −25 to 0 dBFS |

TABLE 6-continued

| Reverberation settings: | |
|---|---|
| Wet to Dry signal ratio | in a range from 0.1 to 20% |
| Damping Freq. Low | in a range from 50 to 500 Hz |
| Damping Freq. High | in a range from 5000 to 14,000 Hz |
| Filter Center Freq. | in a range from 80 to 300 Hz |
| Filter Gain | in a range from −2 to −2 dBFS |
| Filter Type | Shelf |
| Reverb Type | Room |

Avatar Control Group Tests.

In order to determine the actual physiological effects of the reverb, eq and amplitude settings in accordance with at least one embodiment, the present invention tested several groups of individuals in three separate control groups, testing the physiological effects of UMU technology using Avatar computer software and bio-signals.

The Avatar Health Testing system (described at www.a-vatar-health-test-system.com) is a computer software product produced by https://veradyne.com, and based on the work of Heinrich Voll in the 1950's. Avatar results have been correlated in many tests with MRI, blood tests, and other accepted diagnostic tests in Western medicine. One of several advantages of Avatar testing is that it provides instant results with no noise or human sensing (non-invasive) that are repeatable and precisely documented.

Referring to FIGS. 4A and 4B, in the initial tests, three control groups of four people 410, 412, 414 and 416 were tested in the same room, at the same time, using the same musical file, and the same playback equipment. The column 420 of the table indicates the first control group, where no digital sound or music was played to each of the four persons 410, 412, 414 and 416. The column 430 of the table indicates the second control group of four individuals where PCM-processed digital signals, without any specialized UMU processing, were played. The column 440 of the table indicates the third control group of four individuals, where the signals were processed using the UMU processing in accordance with at least one embodiment of the present invention.

As part of the Avatar Health Test, the bio-signal sensors were attached to each of four subjects 410, 412, 414 and 416, in order to measure the Central Nervous System function and responses 451, the liver function and responses 452 and kidney function and responses 453 for each individual in each control group. The bio-signal readings and evaluations were done for four individuals when no audio or sound being provided as input 420 (as a base line). A bio-signal reading was done with regular PCM digital audio signals 430 and then another bio-signal reading and analysis was done with the UMU processed audio signals 440, in accordance with present invention.

For all three bio-signal markers, a reading of 50 is considered optimum for all three measured functions. Readings of over 50 shows irritation or inflammation. Readings of less than 50 indicate dysfunction. After the recording the bio-signals from all three control groups, the results for each individual (in each group) were compared as shown in graphical representations 461, 471, 481 and 491—the base group, 462, 472, 482 and 492, respectively—the regular PCM digital signal group and 463, 473, 483 and 493, respectively—the group receiving the UMU processed signals, respectively shown in FIGS. 4A and 4B.

The base group with no music showed bio-signal readings typically in 60's 70's, 80's. For instance, for the individual 410 in the first control group 420 (with no digital music or audio), the Central Nervous System bio-signal indicator 451 showed a reading at 67.2. For the same individual, the liver function indicator 452 showed a reading of 75.7 and the kidney function indicator 453 showed a reading of 69.7. The readings are for the individual 410 in the first control group are shown graphically in the box 461.

For the same individual in the second control group 430 (with PCM digital signal being provided), the Central Nervous System bio-signal indicator 451 showed a reading of 14.4, the liver function indicator 452 showed a reading of 44.5 and the kidney function indicator 453 showed a reading of 40.0. The bio-signal feedback readings for the individual 410 in the second control group 430 are shown graphically in the box 462. As indicated, all bio-signal indicators show readings well below 50 for this control group.

In comparison, for the same individual 410 in the third control group 440 (where UMU processing has been applied to the digital signals in accordance with at least one embodiment), the Central Nervous System bio-signal indicator 451 showed a reading of 53.9, while the liver function bio-signal indictor 452 showed a reading of 55.5, and the kidney function bio-signal indicator showed a reading of 52.4. The graphical representation of the bio-signal indicators for the first individual 410 using the UMU process of the present invention (the third control group) is shown in the graphical box 463.

Similar readings and comparison was done for individuals 412, 414 and 416 in three control groups. For the second individual 412 in the first control group 420 (base line group, without any audio signal), the Central Nervous System bio-signal sensor 451 showed a reading of 76.9, the liver bio-signal sensor 452 showed a reading of 85.5, and the kidney bio-signal sensor 453, showed a reading of 81.3. This readings are graphically illustrated in the graphical box 471.

For the same individual in the second control group 430 (with PCM digital signal being provided), the Central Nervous System bio-signal indicator showed a reading of 35.2, the liver function indicator showed a reading of 91.1 and the kidney function indicator showed a reading of 29.9. The readings for the individual 412 in the second control group 430 are shown graphically in the box 472. In comparison, for the same individual 412 in the third control group 440 (where UMU processing has been applied to the digital signals in accordance with at least one embodiment), the Central Nervous System bio-signal indicator 451 showed a reading of 51.7, while the liver function bio-signal indictor 452 showed a reading of 55.2, and the kidney function bio-signal indicator showed a reading of 51.0. The graphical readings for the second individual 412 using the UMU process of the present invention is shown in the graphical box 473. Again, this illustrates a much healthier response when using the UMU processing of the present invention.

For the third individual 414 in the first control group 420 (base line group, without any audio signal), the Central Nervous System bio-signal sensor 451 showed a reading of 69.5, the liver bio-signal sensor 452 showed a reading of 73.8, and the kidney bio-signal sensor 453, showed a reading of 74.0. These readings are graphically illustrated in the graphical box 481.

For the same individual 414 in the second control group 430 (with PCM digital signal being provided), the Central Nervous System bio-signal indicator showed a reading of 41.2, the liver function indicator showed a reading of 81.5 and the kidney function indicator showed a reading of 45.7. The readings for the individual 414 in the second control group 430 are shown graphically in the box 482. In comparison, for the same individual 414 in the third control group 440 (where UMU processing has been applied to the digital signals in accordance with at least one embodiment), the Central Nervous System bio-signal indicator showed a reading of 53.8, while the liver function bio-signal indictor showed a reading of 53.4, and the kidney function bio-signal indicator showed a reading of 52.4. The graphical readings for the third individual 414 using the UMU process of the present invention are shown in the graphical box 483. Again, this illustrates a much healthier response when using the UMU processing of the present invention.

For the fourth individual 416 in the first control group 420 (base line group, without any audio signal), the Central Nervous System bio-signal sensor 451 showed a reading of 63.4, the liver bio-signal sensor 452 showed a reading of 79.0, and the kidney bio-signal sensor 453 showed a reading of 80.1. These readings are graphically illustrated in the graphical box 491.

For the same individual 416 in the second control group 430 (with PCM digital signal being provided), the Central Nervous System bio-signal indicator showed a reading of 33.5, the liver function indicator showed a reading of 35.4 and the kidney function indicator showed a reading of 40.1. The readings for the individual 416 in the second control group 430 are shown graphically in the box 492. In comparison, for the same individual 416 in the third control group 440 (where UMU processing has been applied to the digital signals in accordance with at least one embodiment), the Central Nervous System bio-signal indicator showed a reading of 50.1, while the liver function bio-signal indictor showed a reading of 53.0, and the kidney function bio-signal indicator showed a reading of 57.9. The graphical readings for the fourth individual 416 using the UMU process of the present invention is shown in the 493 graphical box. Again, this illustrates a much healthier response when using the UMU processing of the present invention.

To summarize, the Avatar medical test conclusively showed that the bio-signal sensor indications taken from the same individuals, under the same conditions, using the standard PCM digital processing produces far inferior physiological results than the same bio-signal sensor data collected while applying the UMU correction processing in accordance with present invention, using the described equalization, reverberation and volume settings. Thus, the results indicate that listening to music that has been processed with UMU, in accordance with at least one embodiment, is better for human health than not listening to music at all, or using standard PCM digital process for conversion.

The present invention may be applied to all different types of PCM digital audio formats—WAV, AIFF, MP3 and so forth—producing the same better and more beneficial result on the human health when listening to the UMU processed audio signals, which enhance all PCM digital audio formats and reduce or eliminate the negative effects on human physiology (when listening to standard PCM digital music or audio signals).

The above embodiments and illustrative descriptions of the application of the principles of the present invention are intended to enable a person skilled in the art to make or use the disclosed invention. They are not intended to be either exclusive, exhaustive or limiting on the scope of the invention described and claimed herein.

Other variations or modification could be used and applied by a person skilled in the art without deviating from the scope and spirit of the present invention. Such modifications and alternatives arrangements are not intended to be outside the scope of the present invention and are intended to be covered by it. The invention title and abstract are not I hereby claim:

1. A method of processing audio signals comprising:
receiving an analog audio signal as input from at least one source of audio signals;
performing a digital to analog conversion by converting the analog audio signal to a digital format;
performing sampling on the analog audio signal;
processing the digital converted audio signal using a digital system processor, having a computer processor and memory or circuitry, by applying an equalization, a reverberation and a volume setting that is measured to produce an audio output signal that has a more beneficial health response on at least one human physiological functions than an unprocessed PCM digital signal or a base measurement without any audio signal,
measuring the physiological functions of at least one listener using one or more bio-sensors attached to the at least one listener, the sensors configured to measure the at least one improved physiological function of the listener,
wherein the measuring of the physiological functions of the at least one listener using the attached bio-sensors includes measuring the bio-signal responses related to a central nervous system, a liver and a kidney functions of the listener.

2. A method of processing audio signals comprising:
receiving an analog audio signal as input from at least one source of audio signals;
performing a digital to analog conversion by converting the analog audio signal to a digital format;
performing sampling on the analog audio signal;
processing the digital converted audio signal using a digital system processor, having a computer processor and memory or circuitry, by applying an equalization, a reverberation and a volume setting that is measured to produce an audio output signal that has a more beneficial health response on at least one human physiological functions than an unprocessed PCM digital signal or a base measurement without any audio signal,
measuring the physiological functions of at least one listener using one or more bio-sensor attached to the at least one listener, the sensors configured to measure the at least one improved physiological function of the listener,
wherein the bio-sensors attached to the at least one listener indicate bio-signal responses related to the central nervous system, the liver and the kidney function of the listener being in the range of 50-60, when measured using an Avatar health testing bio-sensor measuring system.

3. A method of claim 1, wherein applying the reverberation setting includes applying a reverberation time period in a range from 0.05 to 0.5 seconds, and an HF damping setting in a range of from 6 to 8 kHz.

4. A method of claim 3, wherein applying the reverberation setting includes applying a dry reverberation setting in a range from −0.1 to −2.0 dB, and a wet reverberation setting in a range from −99.9 to −97.9 dB.

5. A method of claim 4, wherein applying the equalization setting includes applying a width of EQ or Q setting at about −0.26, a 40 Hz frequency setting at about +0.2 dB, a 2 kHz frequency setting at about −0.2 dB, and a 12 kHz frequency setting at about +0.2 dB.

6. A method of claim 1, wherein applying the reverberation setting includes applying a pre-delay setting in a range from 40 to 120 ms, a delay time setting is in a range from 0.01 to 0.99 seconds, a direct signal to early signal reference ratio in a range from 20 to 80% and a tail decay in a range from 0.10 to 2.0%.

7. A method of claim 6, wherein applying the reverberation setting includes a wet to dry signal ratio in a range from 0 to 35%, a damping frequency low setting in a range from 50 to 500 Hz, a damping frequency high setting in a range from 5000 to 14,000 Hz, a filter center frequency in a range from 8000 to 16,000 Hz and a filter gain in a range from −4 to −25 dBFS.

8. A method of claim 7, wherein applying the equalization setting includes a gain setting in a range from 0.1 to 1 dB, a center frequency setting in a range from 4000 to 6000 Hz and a quality factor setting in a range from 0.10 to 1.0 Q.

9. A method of claim 6, wherein applying the reverberation setting includes an early reference level in a range from −30.0 to 0 dBFS, a tail level in a range from −25.0 to 0 dBFS, a wet to dry signal ratio in a range from 0.1 to 20%, a damping frequency low setting in a range from 50 to 500 Hz, a damping frequency high setting in a range from 5000 to 14,000 Hz, a filter center frequency in a range from 80 to 300 Hz, and a filter gain in a range from −2 to −2 dBFS.

10. A method of claim 9, wherein applying the equalization setting includes a gain setting in a range from 0.1 to 1 dB, a center frequency setting in a range from 4000 to 6000 Hz and a quality factor setting in a range from 0.10 to 1.0 Q.

11. A method of claim 1, further comprising performing a digital to analog conversion on the processed digital audio signals by converting to analog, and further transmitting the processed audio signal to an output device.

* * * * *